United States Patent [19]

Carabateas et al.

[11] 4,055,588

[45] Oct. 25, 1977

[54] TETRA-(LOWER-ALKYL)3-(3-NITRO-PHENYL)-1,5-PENTANEDIONE-1,2,4,5-TETRACARBOXYLATES

[75] Inventors: Philip M. Carabateas; Gordon L. Williams, both of Schodack, N.Y.

[73] Assignee: Sterling Drug Inc., New York, N.Y.

[21] Appl. No.: 715,329

[22] Filed: Aug. 18, 1976

Related U.S. Application Data

[62] Division of Ser. No. 659,695, Feb. 20, 1976, which is a division of Ser. No. 588,380, June 19, 1975, Pat. No. 3,970,662.

[51] Int. Cl.$^2$ .............................................. C07C 79/46
[52] U.S. Cl. .................................. 560/23; 260/290 R; 260/294.8 R; 260/295.5 R; 260/295.5 S
[58] Field of Search ........................ 260/471 R, 515 P

[56] References Cited

U.S. PATENT DOCUMENTS 3,905,983  9/1975  Bassert et al. ................. 260/295.5 R

*Primary Examiner*—Vivian Garner
*Attorney, Agent, or Firm*—Robert K. Bair; B. Woodrow Wyatt

[57] ABSTRACT

4-(3-Nitrophenyl)pyridine, an intermediate useful in the preparation of 1-(lower-alkyl)-1,4-dihydro-4-oxo-7-(4-pyridyl)-3-quinolinecarboxylates, which are useful as antibacterial agents, is prepared by reacting 3-nitrobenzaldehyde with two molar equivalents of di-(lower-alkyl) oxalacetate (II) in the presence of a catalytic condensing agent, preferably piperidine and/or its acetate, to produce tetra-(lower-alkyl) 3-(3-nitrophenyl)-1,5-pentanedione-1,2,4,5-tetracarboxylate (III), reacting III with ammonia to produce tetra-(lower-alkyl) 1,4-dihydro-4-(3-nitrophenyl)-2,3,5,6-pyridinetetracarboxylate (IV), oxidizing IV to produce tetra-(lower-alkyl) 4-(3-nitrophenyl)-2,3,5,6-pyridinetetracarboxylate (V), hydrolyzing V to produce 4-(3-nitrophenyl)-2,3,5,6-pyridinetetracarboxylic acid (VI) and decarboxylating VI to produce 4-(3-nitrophenyl)pyridine (VI). Intermediates III, IV, V and VI are novel.

2 Claims, No Drawings

TETRA-(LOWER-ALKYL)3-(3-NITROPHENYL)-1,5-PENTANEDIONE-1,2,4,5-TETRACARBOXYLATES

This application is a division of copending application Ser. No. 659,695, filed Feb. 20, 1976, in turn a division of copending application Ser. No. 588,380, filed June 19, 1975 and now U.S. Pat. No. 3,970,662, issued July 20, 1976.

BACKGROUND OF THE INVENTION a. Field of the Invention

This invention relates to processes for the preparation of pyridine-tetracarboxylic acids and to their conversion to the corresponding pyridines, and to intermediates used therein.

b. Description of the Prior Art

A wide variety of synthetic methods for preparing pyridines from acyclic compounds are presented at pages 272 thru 589 of "Pyridine and Its Derivatives, Part I", Klingsberg, Editor, (Interscience Publishers, Inc., New York, 1960). At pages 498-533 under the heading "2-1-2 Condensation", there are presented many illustrations of the "reaction of an aldehyde with ammonia and the second aldehyde or ketone . . . (to produce) a pyridine or its dihydro derivative" (page 498), as given in Tables II-121 thru II-125. In the first complete paragraph of page 500, it is taught:

"Simple aldehydes and ketones without activating groups require mildly forcing conditions and produce the fully aromatic pyridines; accordingly, acetophenone, benzaldehyde, and ammonia in refluxing acetic acid gave a 68% yield of 2,4,6,-triphenylpyridine and a 25% yield of β-phenylpropionophenone."

The first sentence of the next paragraph (page 500) reads:

"The condensation of ammonia and an aldehyde with an active methylenic ketone (The Hantzsch Synthesis) such as ethyl acetoacetate requires only mild conditions and produces a dihydropyridine."

There follows illustrations of the preparation of various lower-alkyl 1,4-dihydro-3,5-pyridinedicarboxylates; however, there is no teaching of the synthesis of any lower-alkyl 1,4-dihydro-2,3,5,6-pyridinetetracarboxylates.

DETAILED DESCRIPTION INCLUSIVE OF PREFERRED EMBODIMENTS

The invention in a process aspect resides in the process of producing 4-(3-nitrophenyl)pyridine (VII) which comprises reacting 3-nitrobenzaldehyde (I) with two molar equivalents of di-(lower-alkyl) oxalacetate (II) in the presence of a catalytic condensing agent, preferably, piperidine and/or its acetate, to produce tetra-(lower-alkyl) 3-(3-nitrophenyl)-1,5-pentanedione-1,2,4,5-tetracarboxylate (III), reacting III with ammonia to produce tetra-(lower-alkyl) 1,4-dihydro-4-(3-nitrophenyl)-2,3,5,6-pyridinetetracarboxylate (IV), oxidizing IV to produce tetra-(lower-alkyl) 4-(3-nitrophenyl)-2,3,5,6-pyridinetetracarboxylate (V), hydrolyzing V to produce 4-(3-nitrophenyl)-2,3,5,6-pyridinetetracarboxylic acid (VI) and decarboxylating VI to produce 4-(3-nitrophenyl)-pyridine (VII). Other process aspects of the invention reside in each of the first, second and fifth steps of the above-described process and various sub-combinations of the five steps including at least one of the said first, second or fifth steps.

The overall process of the invention is illustrated by the following flow sheet:

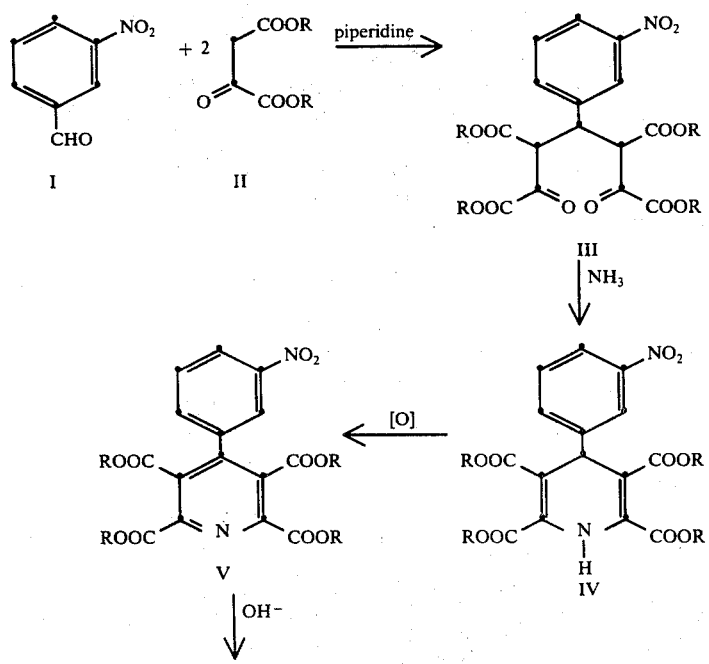

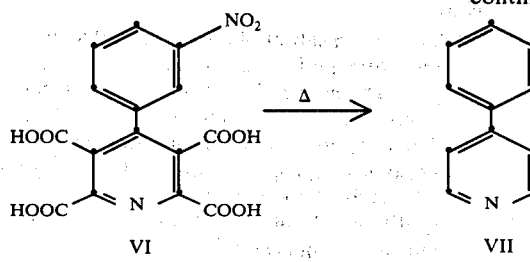

The invention in its composition aspect resides in the compounds of formulas III, IV, V and VI, that is, tetra-(lower-alkyl) 3-(3-nitrophenyl)-1,5-pentanedione-1,2,4,5-tetracarboxylate, tetra-(lower-alkyl) 1,4-dihydro-4-(3-nitrophenyl)-2,3,5,6-pyridinetetracarboxylate, tetra-(lower-alkyl) 4-(3-nitrophenyl)-2,3,5,6-pyridinetetracarboxylate, and 4-(3-nitrophenyl)-2,3,5,6-pyridinetetracarboxylic acid, respectively.

The term "lower-alkyl", as used herein, e.g., as designated by R in formulas II, III, IV and V, means alkyl radicals having from one to six carbon atoms, illustrated by methyl, ethyl, n-propyl, isopropyl, n-butyl, sec.-butyl, tert.-butyl, isobutyl, n-amyl, n-hexyl and the like.

The intermediate compounds of the invention having the formulas IV, V and VI are useful in free base form or in the form of their acid-addition salts, and both forms are within the purview of the invention, and are considered to be one and the same invention. The acid-addition salts are simply a more convenient form for use; and, in practice, use of the salt form inherently amounts to use of the base form. In practicing our invention, we find it convenient to employ the hydrochloride salt. However, other appropriately acceptable salts within the scope of the invention are those derived from mineral acids, such as hydrobromic acid, hydriodic acid, nitric acid, phosphoric acid, sulfamic acid and sulfuric acid; and organic acids, such as acetic acid, tartaric acid, methanesulfonic acid, ethanesulfonic acid, benzenesulfonic acid, and the like, giving the hydrobromide, hydriodide, nitrate, phosphate, sulfamate, sulfate, acetate, tartrate, methanesulfonate, ethanesulfonate and benzenesulfonate, respectively.

The acid-addition salts are prepared preferably by reacting the free base and acid in an organic solvent, e.g., ethanol, acetone, etc., in which the salt separates directly or can be obtained by concentration of the solution.

The molecular structures of said composition aspects of the invention were assigned on the basis of evidence provided by infra red, ultraviolet and nuclear magnetic resonance spectra, by chromatographic mobilities, and by the correspondence of calculated and found values for the elementary analysis for representative examples.

The manner of making and using the instant invention will now be generally described so as to enable a person skilled in the art of pharmaceutical chemistry to make and use the same, as follows:

The reaction of 3-nitrobenzaldehyde with two molar equivalents of di-(lower-alkyl) oxalacetate is preferably carried out by mixing the reactants in the presence of a catalytic condensing agent, preferably piperidine and/or its acetate. The reaction is conveniently carried out by mixing the reactants in a suitable solvent, e.g., ethanol, in the presence of piperidine, piperidine acetate or mixtures thereof. Since the reaction is exothermic, the reactants are conveniently mixed at room temperature, e.g., 25°-30° C., and the reaction temperature rises up to about 35° to 40° C.

The reaction of tetra-(lower-alkyl) 3-(3-nitrophenyl)-1,5-pentanedione-1,2,4,5-tetracarboxylate and ammonia to produce tetra-(lower-alkyl) 1,4-dihydro-4-(3-nitrophenyl)-2,3,5,6-pyridinetetracarboxylate is carried out preferably by heating the reactants in the range of about 30° to 120° C., with a preferred range being 90° to 120° C. The reaction is run preferably in refluxing acetic acid using ammonium acetate as the source of ammonia and using tetraethyl oxalacetate. Other sources of ammonia, e.g., ammonium propionate, or ammonia per se, can be used as well as other solvents in place of acetic acid, e.g., propionic acid, ethanol. The intermediate tetra-(lower-alkyl) oxalacetates are generally known and are either commercially available or prepared by conventional methods.

The oxidation of tetra-(lower-alkyl) 1,4-dihydro-4-(3-nitrophenyl)-2,3,5,6-pyridinetetracarboxylate to yield tetrahydro-(lower-alkyl) 4-(3-nitrophenyl)-2,3,5,6-pyridine-tetracarboxylate is readily carried out using an appropriate oxidizing agent, preferably aqueous nitric acid because of its low cost, ready availability and ease of removal of any excess used. The aqueous nitric acid can contain from about 5 to 50% (by volume) of nitric acid, preferably from about 15-30%. The oxidation can be carried out from about room temperature (25° C.) to about 100° C., preferably from about 50°-70° C. using aqueous nitric acid. Other oxidizing agents and solvents can be used, for example, sodium nitrite in acetic acid, chromium trioxide or sodium dichromate in acetic acid, oxides of nitrogen (nitrogen oxide or nitrogen dioxide), and the like. Alternatively, the reaction can be effected by dehydrogenating the 1,4-dihydro compound by heating it in the presence of a palladium-on-charcoal catalyst, the reaction temperature being in the range of about 100° to 200° C., preferably about 140° to 170° C. and preferably using an appropriate solvent, e.g., mineral oil, xylene, Dowtherm ® A.

The hydrolysis of tetra-(lower-alkyl) 4-(3-nitrophenyl)-2,3,5,6-pyridinetetracarboxylate to produce 4-(3-nitrophenyl)-2,3,5,6-pyridinetetracarboxylic acid is run either under acidic or alkaline conditions, preferably using aqueous hydrochloric acid because of its ready availability, low cost and ease of removal. The hydrolysis can be carried out from about room temperature (25° C.) to about 100° C. using where necessary an appropriate solvent, e.g., ethanol, methanol, acetone, and the like. Other aqueous acidic or alkaline solutions also can be used, e.g., aqueous hydrobromic acid, sulfuric acid, sodium hydroxide, potassium hydroxide, calcium hydroxide, and the like.

The decarboxylation of 4-(3-nitrophenyl)-2,3,5,6-pyridinetetracarboxylic acid to produce 4-(3-nitrophenyl)-pyridine is carried out by heating the tetracarboxylic acid in the absence or presence of a suitable solvent in the range of about 200° to 250° C. The reaction is run preferably at about 220°–230° C. using as a solvent Dowtherm ® A (eutectic mixture of diphenyl and diphenyl ether), mineral oil, or other suitable solvent. The pyridinetetracarboxylic acid can be used in free base form or as its acid-addition salt, e.g., hydrochloride, hydrobromide. Optionally, when the acid-addition salt, e.g., hydrochloride, is used, cuprous oxide is preferably used to take up the hydrogen chloride; alternatively, an acid-acceptor, e.g., potassium carbonate, sodium carbonate, etc., can be used.

The best mode contemplated for carrying out the invention is now set forth as follows:

1. Tetraethyl 3-(3-nitrophenyl)-1,5-pentanedione-1,2,4,5-tetracarboxylate

A mixture containing 207.5 g. of diethyl oxalacetate, 83.2 g. of 3-nitrobenzaldehyde and 1 liter of ethanol was stirred vigorously until most of the aldehyde had dissolved. To the stirred mixture was added a solution containing 25 ml. of piperidine and 40 ml. of acetic acid in 100 ml. of ethanol whereupon temperature rose from 25° to 34° C. and the solution became dark. The reaction mixture was allowed to stand overnight and then heated to 50° C. for 1 hour. There was thus obtained a solution containing tetraethyl 3-(3-nitrophenyl)-1,5-pentanedione-1,2,4,5-tetracarboxylate which can be used directly in the next step (see Example 2) without isolating said 1,5-pentanedione.

Following the procedure described in Example 1 but using in place of diethyl oxalacetate the corresponding molar equivalent quantity of dimethyl, di-n-propyl, diisopropyl, di-n-butyl or di-n-hexyl oxalacetate, there is obtained, respectively, tetramethyl, tetra-n-propyl, tetraisopropyl, tetra-n-butyl or tetra-n-hexyl 3-(3-nitrophenyl)-1,5-pentanedione-1,2,4,5-tetracarboxylate.

2. Tetraethyl 1,4-dihydro-4-(3-nitrophenyl)-2,3,5,6-pyridinetetracarboxylate

To one-half of the solution of Example 1 containing tetraethyl 3-(3-nitrophenyl)-1,5-pentanedione-1,2,4,5-tetracarboxylate was added a warm solution containing 85 g. of ammonium acetate in 400 ml. of acetic acid. The resulting reaction mixture was heated to boiling in an open flask, allowing the ethanol to evaporate off. The reaction mixture was thus concentrated to a dark oil which was made basic with dilute ammonium hydroxide. The ammonium hydroxide solution was extracted with methylene dichloride; the methylene dichloride layer was washed successively with 10% aqueous potassium carbonate, 5% aqueous sodium bisulfite and water, and then dried over anhydrous magnesium sulfate, treated with decolorizing charcoal and filtered. The filtrate was evaporated in vacuo and the residue was taken up in 600 ml. of ether; and, a small amount of insoluble material was filtered off and the filtrate evaporated in vacuo to an oily material which crystallized when stirred with a little ethanol to give 65.7 g. of the product. Evaporation of the ethanol filtrate and trituration of the residue with isopropyl alcohol gave another 13.6 g. of the product. The combined product was recrystallized from ethanol to yield tetraethyl 1,4-dihydro-4-(3-nitrophenyl)-2,3,5,6-pyridinetetracarboxylate, m.p. 121°–124° C.

Following the procedure described in Example 2 but using in place of tetraethyl 3-(3-nitrophenyl)-1,5-pentanedione-1,2,4,5-tetracarboxylate the corresponding molar equivalent quantity of tetramethyl, tetra-n-propyl, tetraisopropyl, tetra-n-butyl or tetra-n-hexyl 3-(3-nitrophenyl)-1,5-pentanedione-1,2,4,5-tetracarboxylate, there is obtained respectively tetramethyl, tetra-n-propyl, tetraisopropyl, tetra-n-butyl or tetra-n-hexyl 1,4-dihydro-4-(3-nitrophenyl)-2,3,5,6-pyridinetetracarboxylate.

3. Tetraethyl 4-(3-nitrophenyl)-2,3,5,6-pyridinetetracarboxylate

A solution of 4.0 ml. of 70% nitric acid in 12 ml. of water was heated to 60° C. and to it was added with stirring 4.21 g. of tetraethyl 1,4-dihydro-4-(3-nitrophenyl)-2,3,5,6-pyridinetetracarboxylate. The reaction mixture was heated with stirring at 60° C. for 1 hour and then poured on ice; the aqueous mixture was extracted with methylene dichloride; and, the extract was dried over anhydrous magnesium sulfate, filtered and evaporated in vacuo to yield an oil which crystallized. The crystalline material was recrystallized from methanol to yield 4.0 g. of tetraethyl 4-(3-nitrophenyl)-2,3,5,6-pyridinetetracarboxylate, m.p. 117°–119° C.

Following the procedure described in Example 3 but using in place of tetraethyl 1,4-dihydro-4-(3-nitrophenyl)-2,3,5,6-pyridinetetracarboxylate the corresponding molar equivalent quantity of tetramethyl, tetra-n-propyl, tetraisopropyl, tetra-n-butyl or tetra-n-hexyl 1,4-dihydro-4-(3-nitrophenyl)-2,3,5,6-pyridinetetracarboxylate, there is obtained, respectively, tetramethyl, tetra-n-propyl, tetraisopropyl, tetra-n-butyl or tetra-n-hexyl 4-(3-nitrophenyl)-2,3,5,6-pyridinetetracarboxylate.

4. 4-(3-Nitrophenyl)-2,3,5,6-pyridinetetracarboxylic acid

A solution of 5.6 g. of potassium hydroxide in 50 ml. of water was added to a solution of tetraethyl 4-(3-nitrophenyl)-2,3,5,6-pyridinetetracarboxylate in 50 ml. of warm ethanol and the resulting reaction mixture was refluxed for two hours and then acidified with dilute aqueous hydrochloric acid. The resulting precipitate was collected and washed successively with water and acetone to yield 6.44 g. of 4-(3-nitrophenyl)-2,3,5,6-pyridinetetracarboxylic acid which can be used in the next step (Example 5) without further purification.

4-(3-Nitrophenyl)-2,3,5,6-pyridinetetracarboxylic acid is also prepared by hydrolyzing tetraethyl 4-(3-nitrophenyl)-2,3,5,6-pyridinetetracarboxylate using aqueous hydrochloric acid as follows: a mixture containing 2.5 g. of tetraethyl 4-(3-nitrophenyl)-2,3,5,6-pyridinetetracarboxylate, 20 ml. of water and 20 ml. of concentrated hydrochloric acid is refluxed with stirring for four hours. The reaction mixture is chilled and the resulting crystallized product was collected to yield 4-(3-nitrophenyl)-2,3,5,6-pyridinetetracarboxylic acid as its hydrochloride.

4-(3-Nitrophenyl)-2,3,5,6-pyridinetetracarboxylic acid is obtained following the procedure described in Example 4 using in place of tetraethyl 4-(3-nitrophenyl)-2,3,5,6-pyridinetetracarboxylate the corresponding respective molar equivalent quantity of tetramethyl, tetra-n-propyl, tetraisopropyl, tetra-n-butyl or tetra-n-hexyl 4-(3-nitrophenyl)-2,3,5,6-pyridinetetracarboxylate.

5. 4-(3-Nitrophenyl)pyridine

A suspension of 6.44 g. of 4-(3-nitrophenyl)-2,3,5,6-pyridinetetracarboxylic acid in 100 ml. of Dowtherm ® A (eutectic mixture of diphenyl and diphenyl ether) was heated to 200° C. with stirring until gas evolution ceased. The reaction solution was cooled and extracted twice with dilute hydrochloric acid; the extracts were washed with ether; and, the acidic solution was basified with ammonium hydroxide. The alkaline mixture was extracted with methylene dichloride; and the extract was dried over anhydrous magnesium sulfate and filtered; and, the dried extract was evaporated in vacuo to remove the solvent. The resulting tan solid was recrystallized from isopropyl acetate to yield 0.8 g. of 4-(3-nitrophenyl)pyridine, m.p. 111°–112° C.

Utilization of 4-(3-nitrophenyl)pyridine in the preparation of the antibacterially active 1-(lower-alkyl)-1,4-dihydro-4-oxo-7-(4-pyridyl)-3-quinolinecarboxylates is described in U.S. Pat. No. 3,753,993, issued Aug. 21, 1973.

We claim:
1. Tetra-(lower-alkyl) 3-(3-nitrophenyl)-1,5-pentanedione-1,2,4,5-tetracarboxylate.
2. Tetraethyl 3-(3-nitrophenyl)-1,5-pentanedione-1,2,4,5-tetracarboxylate according to claim 1.

* * * * *